United States Patent [19]
Lee et al.

[11] Patent Number: 5,699,142
[45] Date of Patent: Dec. 16, 1997

[54] DIFFRACTIVE MULTIFOCAL OPHTHALMIC LENS

[75] Inventors: Chun-Shen Lee, Cupertino, Calif.; Michael J. Simpson, Arlington, Tex.

[73] Assignee: Alcon Laboratories, Inc., Fort Worth, Tex.

[21] Appl. No.: 655,346

[22] Filed: May 23, 1996

Related U.S. Application Data

[63] Continuation-in-part of Ser. No. 299,772, Sep. 1, 1994, abandoned.

[51] Int. Cl.⁶ ............... G02C 7/04; G02B 5/18; A61F 2/16
[52] U.S. Cl. ............... 351/177; 351/161; 351/168; 359/571; 623/6
[58] Field of Search ............... 351/160 R, 160 H, 351/161, 162, 177, 168; 359/565, 571; 623/6

[56] References Cited

U.S. PATENT DOCUMENTS

| | | | |
|---|---|---|---|
| 4,162,122 | 7/1979 | Cohen | 351/161 |
| 4,210,391 | 7/1980 | Cohen | 351/161 |
| 4,338,005 | 7/1982 | Cohen | 351/161 |
| 4,340,283 | 7/1982 | Cohen | 351/161 |
| 4,637,697 | 1/1987 | Freeman | 351/161 |
| 4,641,934 | 2/1987 | Freeman | 351/161 |
| 4,655,565 | 4/1987 | Freeman | 351/161 |
| 4,881,804 | 11/1989 | Cohen | 351/161 |
| 4,881,805 | 11/1989 | Cohen | 351/161 |
| 4,995,714 | 2/1991 | Cohen | 351/161 |
| 4,995,715 | 2/1991 | Cohen | 351/161 |
| 5,017,000 | 5/1991 | Cohen | 351/161 |
| 5,054,905 | 10/1991 | Cohen | 351/161 |
| 5,056,908 | 10/1991 | Cohen | 351/161 |
| 5,076,684 | 12/1991 | Simpson et al. | 351/161 |
| 5,116,111 | 5/1992 | Simpson et al. | 351/161 |
| 5,117,306 | 5/1992 | Cohen | 351/161 |
| 5,120,120 | 6/1992 | Cohen | 351/161 |
| 5,121,979 | 6/1992 | Cohen | 351/161 |
| 5,121,980 | 6/1992 | Cohen | 351/161 |
| 5,129,718 | 7/1992 | Futhey et al. | 351/161 |
| 5,144,483 | 9/1992 | Cohen | 351/161 |
| 5,178,636 | 1/1993 | Silberman | 351/161 |

Primary Examiner—Scott J. Sugarman
Attorney, Agent, or Firm—Jeffrey S. Schira

[57] ABSTRACT

A diffractive, multifocal ophthalmic lens including an apodization zone with echelettes having a smoothly reduced step height to shift the energy balance from the near image to the distant image and thus reduce the glare perceived when viewing a discrete, distant light source.

7 Claims, 5 Drawing Sheets

DIFFRACTIVE MULTIFOCAL OPHTHALMIC LENS

This application is a continuation-in-part of U.S. patent application Ser. No. 08/299,772 filed Sep. 1, 1994, now abandoned.

BACKGROUND OF THE INVENTION

This invention relates generally to the field of ophthalmic lenses and, more particularly, to diffractive multifocal intraocular lenses (IOLs).

The human eye in its simplest terms functions to provide vision by transmitting light through a clear outer portion called the cornea, and focusing the image by way of a lens onto a retina. The quality of the focused image depends on many factors including the size and shape of the eye, and the transparency of the cornea and lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an IOL.

The majority of ophthalmic lenses, including IOLs, currently used are of a monofocal design, (i.e., having a fixed focal length). The focal length of the implanted IOL generally is chosen to optimize vision at 1 meter (−1D spectacle power) from the patient. Thus, most patients receiving an IOL still require glasses for clear distance and near vision with the target of −1D providing variations due to surgical and measurement errors.

Various multifocal ophthalmic lens designs are currently under investigation and these designs generally fall into one of two categories, refractive lenses and diffractive lenses. Diffractive lenses use nearly periodic microscopic structures on the lens to diffract light into several directions simultaneously. This is similar to a diffraction grating and the multiple diffraction orders focus the light into various images corresponding to different focal lengths of the lens. Diffractive multifocal contact lenses and IOLs are more fully discussed in U.S. Pat. Nos. 4,162,122, 4,210,391, 4,338,005, 4,340,283, 4,995,714, 4,995,715, 4,881,804, 4,881,805, 5,017,000, 5,054,905, 5,056,908, 5,120,120, 5,121,979, 5,121,980, 5,144,483, 5,117,306 (Cohen), U.S. Pat. Nos. 5,076,684, 5,116,111 (Simpson, et al.), U.S. Pat. No. 5,129,718 (Futhey, et al.) and U.S. Pat. Nos. 4,637,697, 4,641,934 and 4,655,565 (Freeman), the entire contents of which are incorporated herein by reference.

While a diffractive IOL may have a number of focal lengths, generally, IOLs with only two focal lengths (far and near) are the most common. As with any simultaneous vision multifocal lens, a defocused image (or images) is superimposed on the focused component because of the second lens power, but the defocused image is rarely observed by the user, who concentrates on the detail of interest. Under certain circumstances (for example, at night), the pupil diameter of the user can expand to 5 millimeters (mm) or more, and a discrete distant light source (e.g., automobile headlights or street lights) can appear to be surrounded by a "halo" or "rings". A significant component of the halo is caused by the light that is directed to the near image which becomes defocused at the retina. The visibility of the halo is affected by the diameter of the lens region directing light to the near image, the proportion of total energy directed to the near image, and the overall imaging aberrations of the eye.

In U.S. Pat. No. 4,881,805, Cohen suggests that the intensity of light traveling through a diffractive lens can be varied by reducing the echelette depth at the lens periphery, thus reducing glare (column 4, lines 63–68). Cohen further states that the zone boundary radii of the diffractive zones need to obey the formula:

$$R_m = \sqrt{2mwf}$$

where:
w=the wavelength of light
m=integer representing the mth zone
f=focal length of the 1st order diffraction
Column 5, lines 17–31.

Cohen's theory states that the glare results from the depth of the steps at the diffractive zone boundaries may be more applicable to contact lenses than intraocular lenses. Contact lenses generally move on the eye and the grooves can become filled with debris. In addition, the additive power of the contact lenses generally is less than that of intraocular lenses, which puts the defocused image more in focus, and also the patient's natural residual accommodation may alter the visibility of glare or halos.

Accordingly, a need continues to exist for a diffractive, multifocal IOL that minimizes glare or halos.

BRIEF SUMMARY OF THE INVENTION

The present invention improves upon the prior art by providing a diffractive, multifocal ophthalmic lens having an apodization zone that gradually shifts the energy balance from the near focus to the distance focus over a substantial portion of the lens so that the outer region of the lens directs all of its energy to the distance focus.

Accordingly, one objective of the present invention is to provide a diffractive, multifocal ophthalmic lens having an apodization zone that gradually shifts the energy balance from the near focus to the distance focus over a substantial portion of the lens.

Another objective of the present invention is to provide a diffractive, multifocal ophthalmic lens that reduces glare or halos.

These and other advantages and objectives of the present invention will become apparent from the detailed description and claims that follow.

DETAILED DESCRIPTION OF THE INVENTION

Figure 1A:
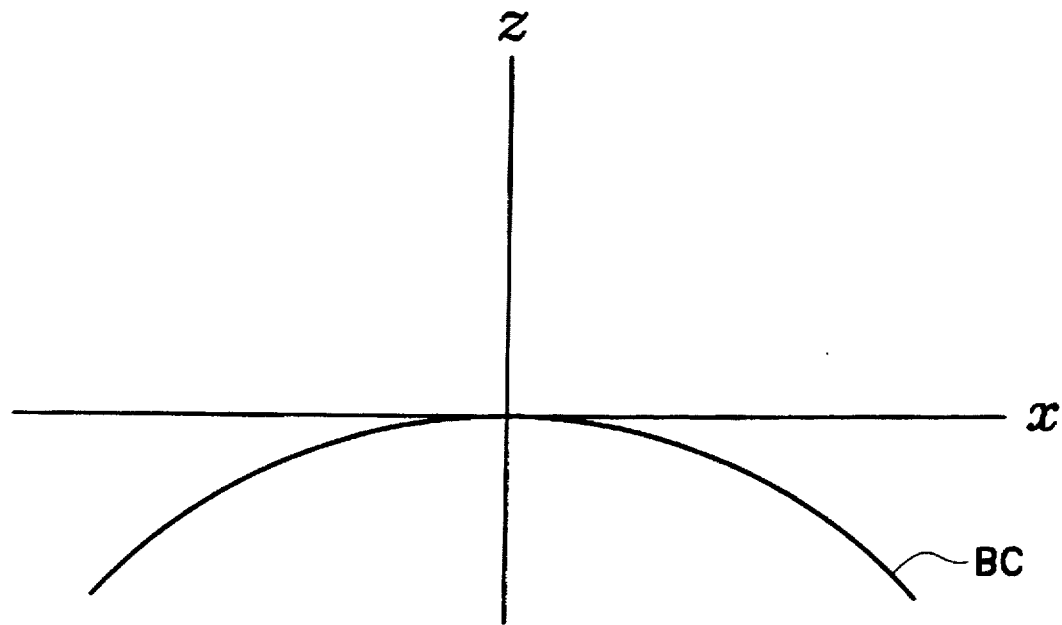
FIG. 1A is a set of Cartesian coordinates placed on the base curve of an ophthalmic lens.

The inventors have discovered that by smoothly decreasing the proportion of energy directed to the near image in a diffractive, multifocal ophthalmic lens, unwanted visual effects (e.g., glare or halos) can be reduced. This smooth decrease in energy is accomplished by gradually reducing the step height of the diffractive structure to zero as the radial distance from the optical axis is increased, causing the lens to become monofocal at the outer periphery of the lens. As a result, all of the energy passing through the outer region of the lens is directed to the distance focus and there is a gradual shift in energy balance between the near focus and the distance focus. This type of design, or "apodization", avoids sharp discontinuities in the wavefront that can produce unwanted diffractive effects.

A better understanding of the present invention may be had by reference to the drawing figures and the geometry associated with the construction of an ophthalmic lens.

The base curve BC of an ophthalmic lens is shown in FIG. 1A. The term "base curve" generally refers to the radius of a spherical 3-D surface. In the preferred embodiment, a base curve having a radius of approximately 28.22 mm has been used. To demonstrate how the location of each point on the ophthalmic lens of the present invention is to be determined and labeled, a set of Cartesian coordinates is placed with its origin at the intersection of the optical axis of the lens and the base curve. Note the horizontal distance from the optical axis is shown along the x-axis and the vertical distance is shown on the z-axis. Thus, the coordinates of each point on the base curve BC may be described with a set of two coordinates which includes either a positive or a negative x-coordinate; but, only a negative z-coordinate.

Figure 1B:
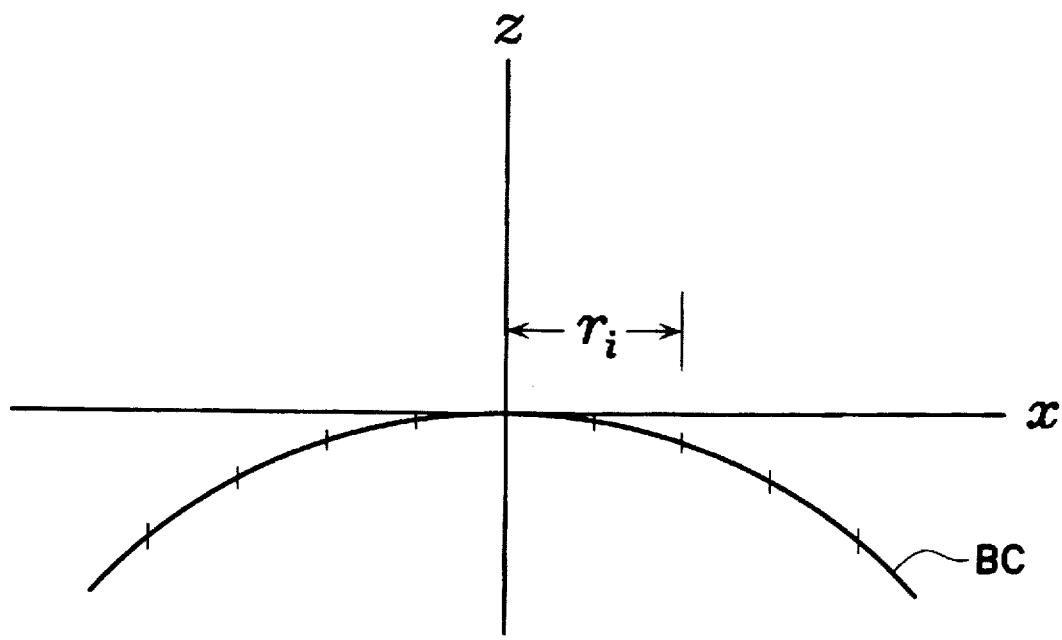
FIG. 1B illustrates the placement of the zone boundary locations on the base curve of an ophthalmic lens.

As a diffractive multifocal ophthalmic lens is characterized by a plurality of annular zones, the next step is to calculate the boundary of each zone with respect to the optical axis. It is at the radial zone boundaries that the steps between the various individual echelettes will be placed. The distance, $r_i$, of each radial zone boundary from the optical axis is given by the equation:

$$r_i^2 = (2i+1)\lambda f \qquad (1)$$

where
i=zone number
λ=design wavelength
f=focal length or $1000/D_{ADD}$ where $D_{ADD}$ is the add power in Diopters Equation (1) is a special case of the more general equation:

$$r_i^2 = r_0^2 + 2i\lambda f \qquad (2)$$

where the radius of the central zone of the ophthalmic lens is set to $r_0^2 = \lambda f$. In the preferred embodiment the design wavelength, λ, is set at 550 nm green light at the center of the visual response and the add power is set at 4 Diopters. The calculation of each $r_i$ produces the series of zone boundary radii along the base curve as shown in FIG. 1B.

Figure 1C:
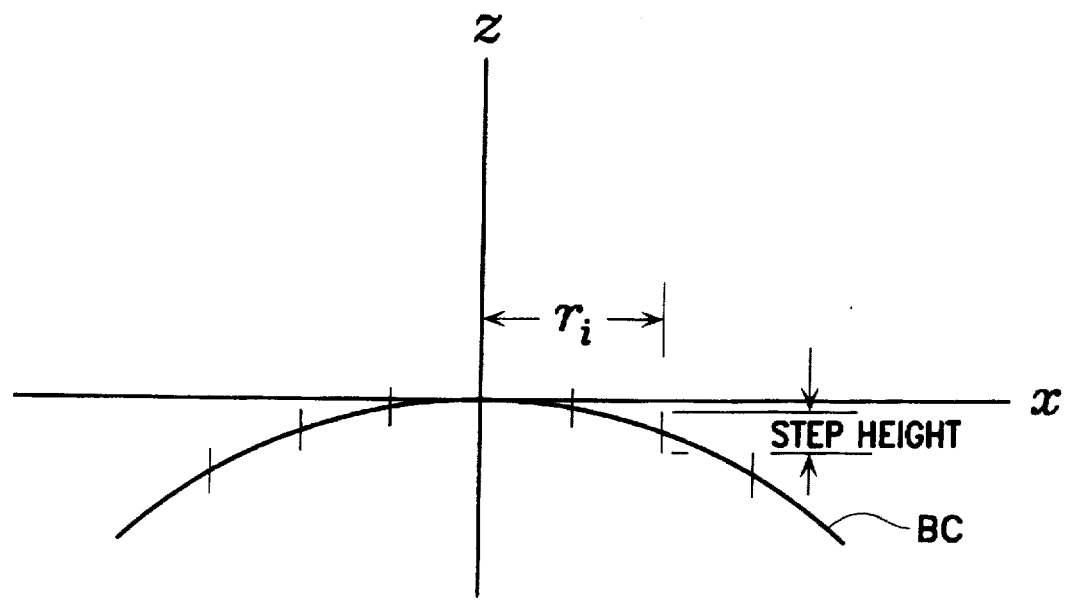
FIG. 1C illustrates the placement of step heights at each zone boundary location.

To establish the step height or vertical height of each individual echelette at each zone boundary point on the base curve, the following equation is used.

where:

$$\text{Step height} = \frac{p\lambda}{(n_2 - n_1)} \qquad (3)$$

p=phase height
λ=design wavelength
$n_2$=refractive index of the lens
$n_1$=refractive index of aqueous In the preferred embodiment, the phase height is given the value of 0.5, $n_2$ is given the value 1.5542 and $n_1$ is given the value 1.336. As shown in FIG. 1C, the calculated constant step height is centered on each zone boundary so that half of the step height lies above the base curve and the other half of the step height lies beneath the base curve.

Figure 1D:
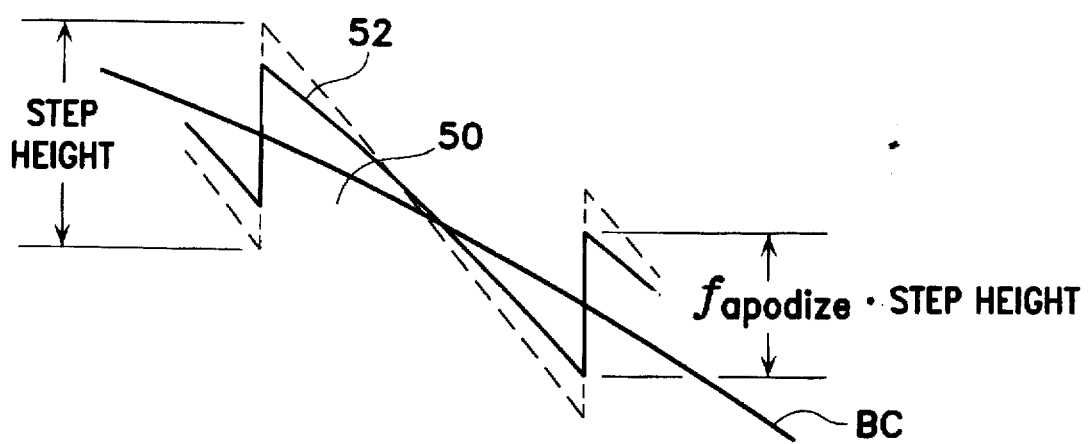
FIG. 1D illustrates the reduction in step heights caused by application of the apodization factor to each step height.

In the present invention it has been found that by progressively reducing the step height of a selected group of individual echelettes 50 by a predetermined amount, the unwanted effects of glare perceived as a halo or rings around a distant, discrete light source will be substantially reduced. The selected group of individual echelettes to be reduced in step height are all contained in what is termed an apodization zone. The progressive systematic individual reduction of step height is shown in FIG. 1D.

To determine the reduced step height to be centered on the base curve BC, the step height calculated in Equation (3) above is multiplied by an apodization factor, $f_{apodize}$, calculated for each individual echelette. These apodization factors are determined by the following equation.

$$f_{apodize} = 1 - \left\{ \frac{(r_i - r_{in})}{(r_{out} - r_{in})} \right\}^{exp}, r_{in} \leq r_i \leq r_{out} \qquad (4)$$

where:
$r_i$=the distance of each radial zone boundary from the optical axis or the x-coordinate of each step height position
$r_{in} = r_i$ at the inner boundary of the apodization zone
$r_{out} = r_i$ at the outer boundary of the apodization zone
exp=a value chosen based on the relative location of the apodization zone from the optical axis and the desired reduction in echelette step height Therefore, as the value of $r_i$ increases in equation (4), the numerator of the fraction will increase which causes the quantity subtracted from 1 to increase to where its numerical value approaches 1. Thus, the value of $f_{apodize}$ will approach zero. Therefore, when $f_{apodize}$ is multiplied by the step height, the step height, will similarly approach 0.

Figure 2A:
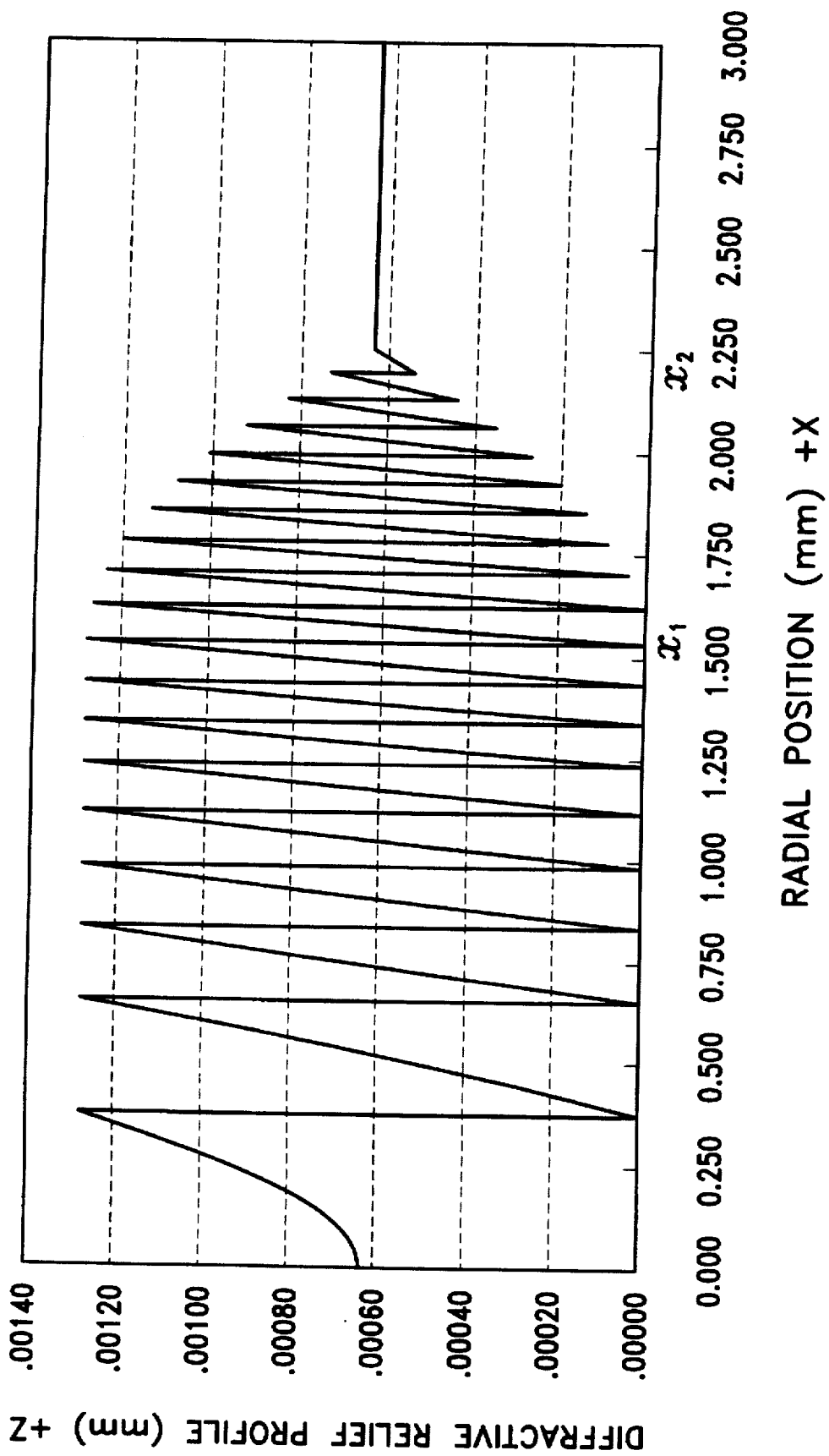
FIG. 2A is a graph of the diffractive relief profile, which is the difference between the vertical height or the z-axis location of each point on the echelette surface of the lens and the vertical height or the z-axis position of the corresponding point on the base curve, plotted against radial position from the optical axis of the lens for a first embodiment of the present invention.
Figure 2B:
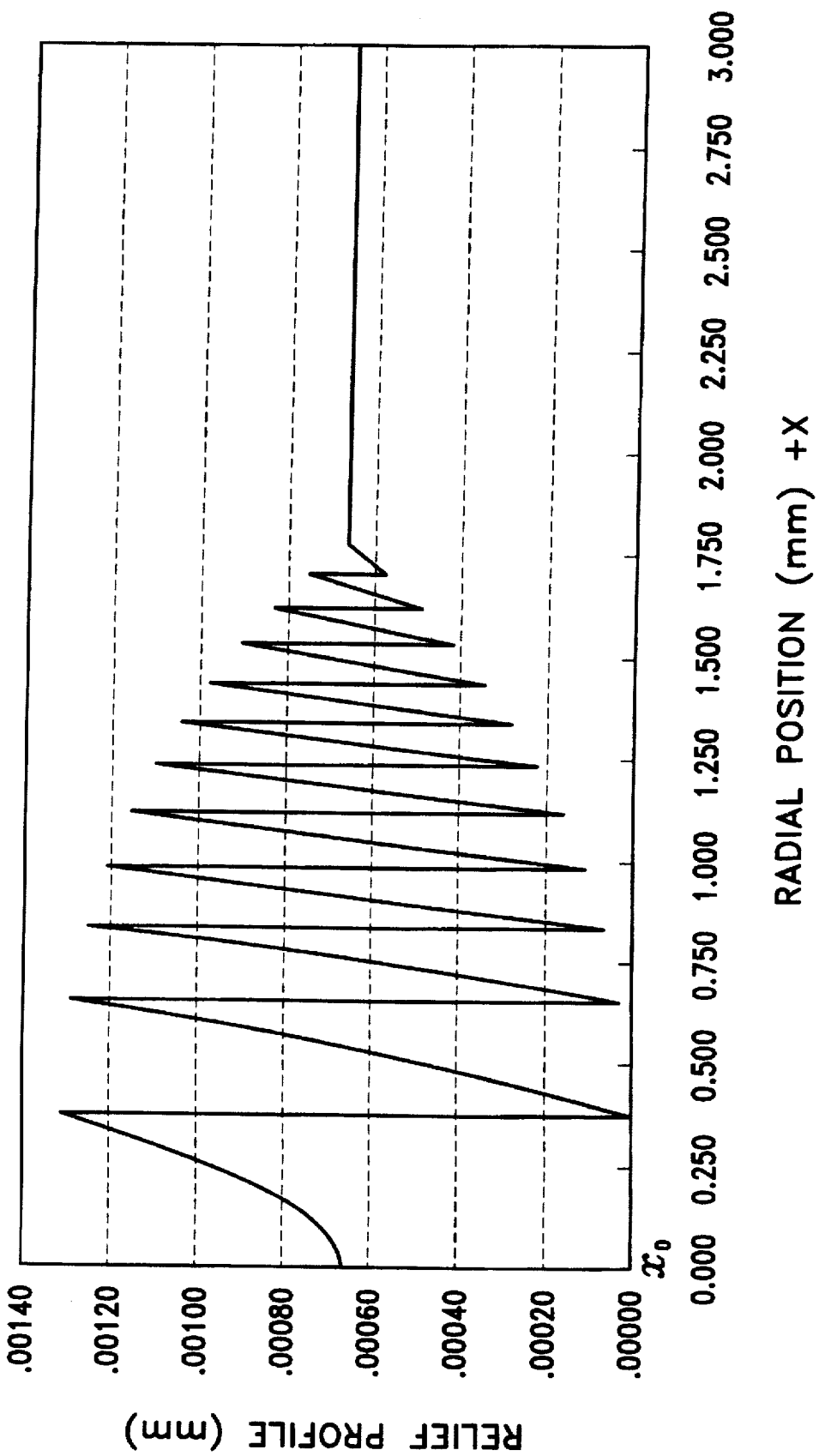
FIG. 2B is a graph of the diffractive relief profile, plotted against radial position from the optical axis of the lens for a second embodiment of the present invention.

In one embodiment of the invention, the first nine zones or echelettes surrounding the optical axis all have the same step height, and exp=2 for apodization between the 9th and 19th zones (FIG. 2A). In another embodiment of the invention it has been shown that the value of "exp" may be in a range between approximately 3 and approximately 6.2 where the apodization reduction in step height begins at the optical axis (FIG. 2B).

Now that the zone boundary points along the base curve BC are known and the reduced step heights to be located at each of these points are known, the next step is to determine the location of the points which lie on the spherical echelette surface 52 (FIG. 1D) which connects the top of a modified echelette step height to the bottom of the next modified echelette step height at the next zone boundary farther away from the optical axis. Each spherical surface 52 has a different center and a different radius. The distance $Z_{rad}$ of the center of each spherical surface 52 from the origin (FIG. 1A) on the z-axis is given according to the following equation.

$$Z_{rad} = \frac{(r_{in}^2 + z_{in}^2) - (r_{out}^2 + z_{out}^2)}{2(z_{in} - z_{out})} \quad (5)$$

where:

$z_{in}$=z-coordinate at $r_{in}$ $z_{out}$=z-coordinate at $r_{out}$

The radius $R_{rad}$ of each spherical surface beginning at each center calculated according to equation (5) is given by the following equation.

$$R_{rad} = \sqrt{(z_{in} - Z_{rad})^2 + r_{in}^2} \quad (6)$$

Having calculated the location of each zone boundary, the reduced step heights at each zone boundary, the centers and the radii for each spherical surface between the zone boundaries, it is now possible using conventional techniques to express and plot each point on the diffractive surface of an ophthalmic lens in terms of its x-coordinate and its z-coordinate pursuant to the Cartesian coordinate scheme shown in FIG. 1A.

To best illustrate the impact of the application of $f_{apodize}$ determined in equation (4) on the height of each individual echelette and how $f_{apodize}$ may be applied in selected regions or zones of the diffractive surface, it is instructive to plot the difference between the z-coordinate of the diffractive surface and the z-coordinate of the base curve against the corresponding x-coordinate. If there is no difference or a constant difference between the z-coordinate of the diffractive surface and the z-coordinate of the base curve, the resulting difference curve will be flat, thus reflecting a constant value. At the points of maxima difference between the z-coordinate on the diffractive surface and the z-coordinate of the base curve, the difference curve will show its greatest spikes. Where the differences between the z-coordinate on the diffractive surface and the z-coordinate of the base curve begin to diminish, the spikes will show a reduction in size according to the pattern of echelette step height reduction. Thus where the step height is reduced in size, according to a predetermined formula, it can be expected that spikes of reduced size will appear.

By reference to FIG. 2A it will be seen that there is no reduction in the difference between the z-coordinate of the diffractive surface and the z-coordinate of the base curve over the first 9 zones or echelettes in one embodiment. After the 9th echelette the apodization zone begins; that is, $f_{apodize}$ is applied and the difference between the z-coordinate of the diffractive surface and the z-coordinate of the base curve is progressively reduced to a constant value as shown at the far right hand end of the plot. The selected group of echelettes having a reduced stepped height are contained in a region of the ophthalmic lens called the apodization zone.

A second embodiment is plotted in FIG. 2B where the reduction in the difference between the z-coordinate of the diffractive surface and the z-coordinate of the base curve begins at the optical axis and progresses toward the periphery of the lens, resulting in a flat line on the far right hand end of the plot.

Figure 3A:
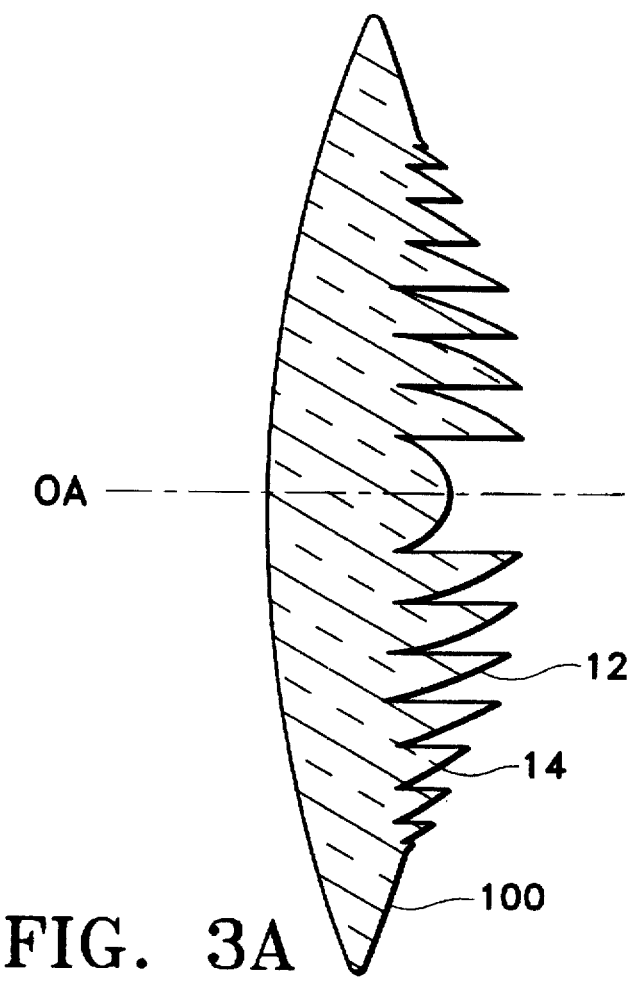
FIG. 3A is a representative cross sectional view of an ophthalmic lens made according to the echelette step height profile shown in FIG. 2A.

A cross sectional representative view of lens 100 having a series of echelettes similar to the one depicted in FIG. 2A is shown in FIG. 3A. Note that the step height of the echelettes 12 surrounding the optical axis OA remains constant over several echelettes 12 before it begins to reduce in size. Then, as the distance of each individual echelette from the optical axis OA increases the step height of each echelette 14 approaches zero as indicated above in the discussion explaining equation (4).

Figure 3B:
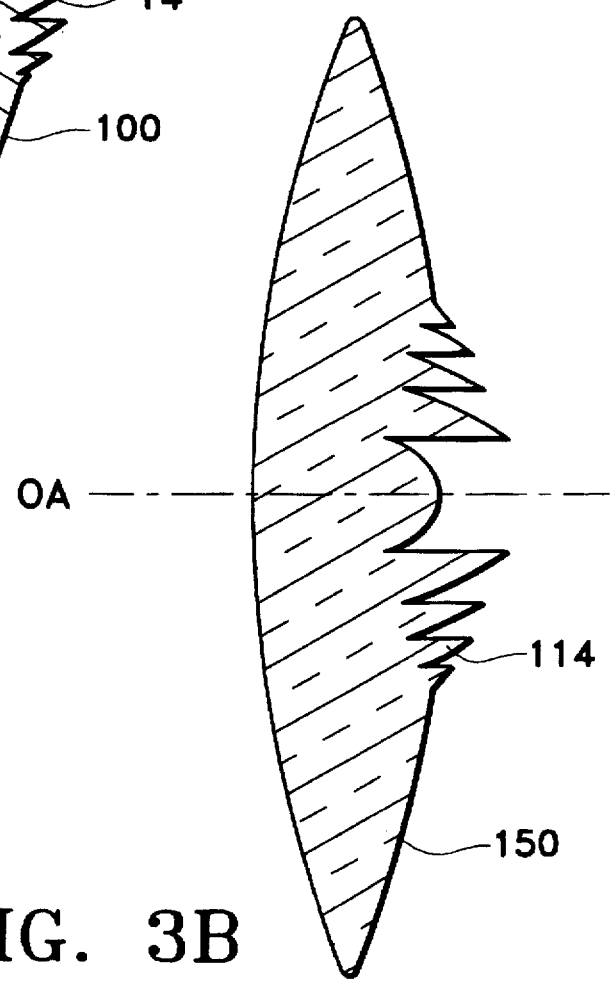
FIG. 3B is a representative cross sectional view of an ophthalmic lens made according to the echelette step height profile shown in FIG. 2B.

A cross sectional view of lens 150 having a series of echelettes 114 similar to the one depicted in FIG. 2B is shown in FIG. 3B. Note that the height of the echelettes 114 surrounding the optical axis OA begins diminishing with the increase in the distance of the echelette 114 from the optical axis OA.

Algebraically, the following set of equations can be used to model the ophthalmic lens shown in FIG. 2A.

$$\text{if } 0 \leq r_i \leq r_{in}, \text{ then } f_{apodize} = 1 \quad (7)$$

$$\text{if } r_{in} < r_i \leq r_{out}, \text{ then } f_{apodize} = 1 - \left(\frac{(r_i - r_{in})}{(r_{out} - r_{in})}\right)^2 \quad (8)$$

From equations (7) and (8), it may be seen that there is no reduction in echelette step height between the optical axis and $r_{in}$. Between $r_{in}$ and $r_{out}$ each echelette step height is reduced by progressively smaller apodization factors.

Similarly, the following set of equations may be used to model the ophthalmic lens shown in FIG. 2B.

$$\text{if } 0 \leq r_i \leq r_{out}, \text{ then } f_{apodize} = 1 - \left(\frac{r_i}{r_{out}}\right)^3 \quad (9)$$

$$\text{if } r_{out} < r_i, \text{ then } f_{apodize} = 1 \quad (10)$$

From equations (9) and (10), it may be seen that the reduction in echelette step height begins at the optical axis and proceeds to $r_{out}$. As previously indicated, the exponent in the equation for $f_{apodize}$ may be as high as approximately 6.2.

The foregoing examples are illustrative only. The present invention is not to be limited by any specific modulation function or functions. Both the reduction in the step height and the location of the apodization zone boundaries can be selected according to the optical aberrations inherent in the optical system selected. The present invention is also not to be limited to a particular surface relief structure. Other diffractive lens methods may be used to make the ophthalmic lens of the present invention. Such structures and methods shall be included within the scope and meaning of the appended claims.

We claim:

1. A method of reducing the glare associated with a diffractive, multifocal ophthalmic lens producing a distant image and a near image, the diffractive, multifocal ophthalmic lens having a plurality of echelettes located at a radius $r_i$ from an optical axis of the lens, each of the echelettes having a step height, the method comprising the steps of:

a) selecting a base curve;

b) calculating the position, $r_i$, of each echelette with respect to the base curve;

c) choosing the step height for each echelette; and d) progressively reducing the step height of each echelette by an apodization factor $f_{apodize}$ in a selected apodization zone, the reduction in the step height increasing for each echelette in the apodization zone as the distance of each echelette from the optical axis increases;

whereby the glare associated with a diffractive, multifocal ophthalmic lens is reduced by shifting the energy balance between the near image and the distant image by smoothly reducing the step height of each echelette in the apodization zone.

2. The method of claim 1 wherein the apodization zone is between a zone of echelettes of substantially uniform step height and a periphery of the diffractive, multifocal ophthalmic lens.

3. The method of claim 2 wherein the progressive reduction in step height of each echelette in the apodization by the apodization factor $f_{apodize}$ is determined by the following equation:

$$f_{apodize} = \cdot \left[ 1 - \left\{ \frac{(r_i - r_{in})}{(r_{out} - r_{in})} \right\}^2 \right]$$

where:

$r_{in} = r_i$ at the inner boundary of the apodization zone
$r_{out} = r_i$ at the outer boundary of the apodization zone.

4. The method of claim 1 wherein the apodization zone begins at the optical axis and progresses outwardly toward a periphery of the diffractive, multifocal ophthalmic lens and the apodization factor $f_{apodize}$ used to progressively reduce in the step height of each echelette is determined by the following equation:

$$f_{apodize} = \cdot \left[ 1 - \left( \frac{(r_i)}{(r_{out})} \right)^3 \right]$$

where $r_{out} = r_i$ at the outer boundary of the apodization zone.

5. An ophthalmic lens, comprising: an optic having a plurality of echelettes, each echelette being located at a radius $r_i$ from the optical axis and having a step height progressively reduced by an apodization factor $f_{apodize}$, the apodization factor being determined by the following equation:

$$f_{apodize} = \cdot \left[ 1 - \left( \frac{(r_i)}{(r_{out})} \right)^3 \right]$$

where $r_{out} = r_i$ at the outer boundary of the apodization zone.

6. An ophthalmic lens, comprising: an optic with a plurality of echelettes, each echelette being located in an apodization zone, the apodization zone beginning at a radius $r_i$ from the optical axis and having a step height progressively reduced by an apodization factor $f_{apodize}$, the apodization factor being determined by the following equation:

$$f_{apodize} = \cdot \left[ 1 - \left( \frac{(r_i - r_{in})}{(r_{out} - r_{in})} \right)^2 \right]$$

where $r_{in} = r_i$ at the inner boundary of the apodization zone; and $r_{out} = r_i$ at the outer boundary of the apodization zone.

7. A method of reducing the glare associated with a diffractive, multifocal ophthalmic lens having a distance focus and a near focus, the diffractive, multifocal ophthalmic lens having a plurality of echelettes located at a radius $r_i$ from an optical axis, each of the echelettes having a step height, the method comprising the step of providing an apodization zone that gradually shifts the energy balance between the near focus and the distance focus by progressively increasing the reduction in the step height of each echelette by an apodization factor, $f_{apodize}$, as the radius $r_i$ from the optical axis increases according to the following equation:

$$f_{apodize} = \cdot \left[ 1 - \left( \frac{(r_i - r_{in})}{(r_{out} - r_{in})} \right)^{exp} \right]$$

where:

$r_{in} = r_i$ at the inner boundary of the apodization zone
$r_{out} = r_i$ at the outer boundary of the apodization zone
approx. $3 \leq exp \leq$ approx. $6.2$.

* * * * *